US010663445B2

(12) United States Patent
Wang et al.

(10) Patent No.: US 10,663,445 B2
(45) Date of Patent: May 26, 2020

(54) METHOD AND SYSTEM FOR IDENTIFYING PLANT SPECIES BASED ON HYPERSPECTRAL DATA

(71) Applicant: Beijing Normal University, Beijing (CN)

(72) Inventors: Guoqiang Wang, Beijing (CN); Puze Wang, Beijing (CN); Yanbo Peng, Beijing (CN); Ruimin Li, Beijing (CN); Tingxi Liu, Beijing (CN); Wei Wang, Beijing (CN); Yinglan A, Beijing (CN)

( * ) Notice: Subject to any disclaimer, the term of this patent is extended or adjusted under 35 U.S.C. 154(b) by 214 days.

(21) Appl. No.: 15/972,184

(22) Filed: May 6, 2018

(65) Prior Publication Data

US 2019/0339242 A1    Nov. 7, 2019

(51) Int. Cl.
*G01N 33/00* (2006.01)
*G01N 21/17* (2006.01)
*G06K 9/00* (2006.01)
*G01J 3/28* (2006.01)

(52) U.S. Cl.
CPC ........ *G01N 33/0098* (2013.01); *G01J 3/2823* (2013.01); *G01N 21/17* (2013.01); *G06K 9/00147* (2013.01); *G06K 9/00657* (2013.01); *G01J 2003/2826* (2013.01); *G01N 2021/1797* (2013.01)

(58) Field of Classification Search
CPC ............... G01N 33/0098; G01N 21/17; G01N 2021/1797; G01N 21/274; G01N 23/223; G01N 1/08; G01J 3/2823; G01J 2003/2826; G01J 3/28; G01J 2003/2866; G06K 9/00147; G06K 9/00657; G06T 7/41; G06T 7/0012
See application file for complete search history.

(56) References Cited

U.S. PATENT DOCUMENTS

2005/0151965 A1* 7/2005 Bissett, III ................ G01J 3/28
356/328
2014/0369568 A1* 12/2014 Mangoubi ................. G06T 7/41
382/108
2018/0188225 A1* 7/2018 Viscarra Rossel ... G01N 23/223

OTHER PUBLICATIONS

EPO—PLS, Roger et al, 2003 https://reader.elsevier.com/reader/sd/pii/S0169743903000510?token=2409FF3970B842DAD43C2D9B80EACF0708FD344BD6B10C6801C44A8A95F467617400C2C092B64C1849085DB3C94F7C0F (Year: 2003).*

* cited by examiner

*Primary Examiner* — Jianxun Yang
(74) *Attorney, Agent, or Firm* — W&K IP (57) ABSTRACT

The present disclosure provides a method and system for identifying plant species based on hyperspectral data, wherein the method includes: performing atmospheric radiation correction for the hyperspectral data of plants to be identified adopting Linear Regression method, to obtain corrected hyperspectral data, wherein, the hyperspectral data of the plants to be identified are collected by a hyperspectral ground object spectrometer provided within an unmanned aerial vehicle (UAV); performing external parameter orthogonalisation (EPO) processing for the corrected hyperspectral data; performing first order differential processing for the EPO processed hyperspectral data, to obtain hyperspectral data highlighting absorption peak information; performing discrete wavelet transformation processing for the hyperspectral data highlighting the absorption peak information, to obtain wavelet coefficients corresponding to the plants to be identified.

8 Claims, 4 Drawing Sheets system for identifying plant species based on hyperspectral data performing by a controller atmospheric radiation correction for the hyperspectral data of plants to be identified adopting Linear Regression method, to obtain corrected hyperspectral data, wherein, the hyperspectral data of the plants to be identified are collected by a hyperspectral ground object spectrometer provided within an unmanned aerial vehicle(UAV) — 101 performing by the controller external parameter orthogonalisation(EPO) processing for the corrected hyperspectral data, to obtain EPO processed hyperspectral data — 102 performing by the controller first order differential processing for the EPO processed hyperspectral data, to obtain hyperspectral data highlighting absorption peak information — 103 performing by the controller discrete wavelet transformation processing for the hyperspectral data highlighting the absorption peak information by adopting discrete wavelet transformation, to obtain wavelet coefficients corresponding to the plants to be identified — 104 obtaining by the controller a set of physiological characteristic parameters corresponding to the plants to be identified according to the wavelet coefficients corresponding to the plants to be identified and a preset quantitative inversion model, wherein the set of physiological characteristic parameters includes at least one physiological characteristic parameter — 105 determining by the controller plant species corresponding to the set of physiological characteristic parameters according to a preset plant database, wherein the plant database includes a set of physiological characteristic parameters corresponding to different plant species — 106

Figure 1

| | |
|---|---|
| preprocessing by the controller hyperspectral data of plants to be studied, to obtain wavelet coefficients corresponding to the plants to be studied, wherein the plants to be studied are plants of known plant species | 201 |
| performing by the controller multiple regression fitting processing using the wavelet coefficients corresponding to the plants to be studied as independent variables, and the set of physiological characteristic parameters corresponding to the plants to be studied, obtained through the biochemistry experiments as dependent variables, to obtain the quantitative inversion model | 202 |
| performing by the controller atmospheric radiation correction for the hyperspectral data of plants to be identified by adopting Linear Regression method, to obtain corrected hyperspectral data, wherein, the hyperspectral data of the plants to be identified are collected by the hyperspectral ground object spectrometer provided within an unmanned aerial vehicle(UAV) | 203 |
| performing by the controller EPO processing for the corrected hyperspectral data, to obtain EPO processed hyperspectral data | 204 |
| performing by the controller first order differential processing for the EPO processed hyperspectral data, to obtain hyperspectral data highlighting an absorption peak information | 205 |
| performing by the controller discrete wavelet transformation processing for the hyperspectral data highlighting the absorption peak information by adopting discrete wavelet transformation, to obtain wavelet coefficients corresponding to the plants to be identified | 206 |
| obtaining by the controller the set of physiological characteristic parameters corresponding to the plants to be identified according to the wavelet coefficients of the plants to be identified and a preset quantitative inversion model, wherein the set of physiological characteristic parameters includes at least one physiological characteristic parameter | 207 |
| determining by the controller plant species corresponding to the set of physiological characteristic parameters according to a preset plant database, wherein the plant database includes a set of physiological characteristic parameters corresponding to different plant species | 208 |

METHOD AND SYSTEM FOR IDENTIFYING PLANT SPECIES BASED ON HYPERSPECTRAL DATA

TECHNICAL FIELD

The disclosure relates to the technical field of engineering measurement, in particular to a method and system for identifying plant species based on hyperspectral data.

BACKGROUND

With more and more attention having been paid to protection of plants and protection of the natural environment, the research of plant species receives more and more attention.

In prior art, the roots, stems and leaves of plants can be analyzed in the laboratory by using biochemical determination method, to obtain the physiological characteristic parameters of plants, for example, chlorophyll content and nitrogen content of leaves and so on. Then, information for plant species can be obtained by biochemical determination method.

However, in prior art, the way of obtaining the information for plant species using biochemical determination method needs long time experimental analysis, thus the efficiency for analysis is low.

SUMMARY

The disclosure provides a method and system for identifying plant species based on hyperspectral data, so as to solve the problem that it needs long-time experimental analysis to determine plant species in prior art, and thus the efficiency for analysis is low.

One aspect of the present disclosure is to provide a method for identifying plant species based on hyperspectral data, including:

performing by a controller atmospheric radiation correction for the hyperspectral data of plants to be identified adopting Linear Regression method, to obtain corrected hyperspectral data, wherein, the hyperspectral data of the plants to be identified are collected by a hyperspectral ground object spectrometer provided within an unmanned aerial vehicle (UAV);

performing by the controller external parameter orthogonalisation (EPO) processing for the corrected hyperspectral data, to obtain EPO processed hyperspectral data;

performing by the controller first order differential processing for the EPO processed hyperspectral data, to obtain hyperspectral data highlighting absorption peak information;

performing by the controller discrete wavelet transformation processing for the hyperspectral data highlighting the absorption peak information by adopting discrete wavelet transformation, to obtain wavelet coefficients corresponding to the plants to be identified;

obtaining by the controller a set of physiological characteristic parameters corresponding to the plants to be identified according to the wavelet coefficients corresponding to the plants to be identified and a preset quantitative inversion model, wherein the set of physiological characteristic parameters includes at least one physiological characteristic parameter; and determining by the controller plant species corresponding to the set of physiological characteristic parameters according to a preset plant database, wherein the plant database includes a set of physiological characteristic parameters corresponding to different plant species.

Further, performing by the controller atmospheric radiation correction for the hyperspectral data of plants to be identified adopting Linear Regression method, to obtain corrected hyperspectral data includes:

determining by the controller the corrected hyperspectral data according to the hyperspectral data, i.e. $DN=k*R+b$, wherein R is the hyperspectral data, and k and b are constant coefficients respectively.

Further, performing by the controller EPO processing for the corrected hyperspectral data, to obtain EPO processed hyperspectral data includes:

determining by the controller a projection matrix P according to a spectral matrix, i.e. $X=XP+XQ+R$, wherein, X is a matrix of the corrected hyperspectral data, P is a projection matrix for information that is useful for data prediction in the corrected hyperspectral data, Q is a projection matrix for information that is useless for data prediction in the corrected hyperspectral data, and R is a preset residual matrix; and determining by the controller a orthogonalisation matrix according to the matrix X of the corrected hyperspectral data and the projection matrix P, i.e. $X^*=XP$, and determining that the orthogonalisation matrix $X^*$ is the EPO processed hyperspectral data.

Further, before the controller obtains the set of physiological characteristic parameters corresponding to the plants to be identified according to the wavelet coefficients corresponding to the plants to be identified and the preset quantitative inversion model, the method further includes:

preprocessing by the controller the hyperspectral data of plants to be studied, to obtain wavelet coefficients corresponding to the plants to be studied, wherein the plants to be studied are plants of known plant species; and performing by the controller multiple regression fitting processing using the wavelet coefficients corresponding to the plants to be studied as independent variables, and the set of physiological characteristic parameters corresponding to the plants to be studied, obtained through the biochemistry experiments as dependent variables, to obtain the quantitative inversion model.

Further, preprocessing by the controller the hyperspectral data of plants to be studied, to obtain wavelet coefficients corresponding to the plants to be studied includes:

performing by the controller atmospheric radiation correction for the hyperspectral data of plants to be studied by adopting Linear Regression method, to obtain corrected hyperspectral data of plants to be studied;

performing by the controller EPO processing for the corrected hyperspectral data of the plants to be studied, to obtain EPO processed hyperspectral data of the plants to be studied;

performing by the controller first order differential processing for the EPO processed hyperspectral data of the plants to be studied, to obtain hyperspectral data of the plants to be studied highlighting the absorption peak information; and performing by the controller discrete wavelet transform processing for the hyperspectral data of the plants to be studied highlighting the absorption peak information by adopting discrete wavelet transformation, to obtain wavelet coefficients corresponding to the plants to be studied.

Further, an attitude and position measuring device is further arranged within the UAV.

Accordingly, before the controller performs atmospheric radiation correction for the hyperspectral data of plants to be identified by adopting Linear Regression method, to obtain corrected hyperspectral data, the method further includes:

receiving by the attitude and position measuring device a first trigger instruction sent by the controller, and conducting navigation and positioning of the UAV according to the first trigger instruction, such that the UAV arrives at a preset locating position;

sending by the controller collecting instruction to the hyperspectral ground object spectrometer after determining that the UAV has arrived at the preset locating position; and collecting by the hyperspectral ground object spectrometer the hyperspectral data of the plants to be identified according to the collecting instruction.

Further, sending by the controller collecting instruction to the hyperspectral ground object spectrometer after determining that the UAV has arrived at the preset locating position includes:

sending by the controller a second trigger instruction to the data storage device after determining that the UAV has arrived at the preset locating position;

generating by the data storage device the collecting instruction according to the second trigger instruction, and sending the collecting instruction to the hyperspectral ground object spectrometer;

collecting by the hyperspectral ground object spectrometer the hyperspectral data of the plants to be identified according to the collecting instruction includes:

collecting by the hyperspectral ground object spectrometer hyperspectral data of the plants to be identified and information of the hyperspectral ground object spectrometer according to the collecting instruction, and sending the hyperspectral data of the plants to be identified and the information of the hyperspectral ground object spectrometer to the data storage device; and storing by the data storage device the hyperspectral data of the plants to be identified and the information of the hyperspectral ground object spectrometer.

Further, after the hyperspectral ground object spectrometer collects the hyperspectral data of the plants to be identified according to the collecting instruction, the method further includes:

collecting by the hyperspectral ground object spectrometer hyperspectral data of black-and-white board on the ground;

rectifying by the data storage device the hyperspectral data of the plant to be identified according to the hyperspectral data of the black-and-white board on the ground.

The other aspect of the present disclosure is to provide a system for identifying plant species based on hyperspectral data, including a controller:

the controller includes:

a correction module, configured to perform atmospheric radiation correction for the hyperspectral data of plants to be identified adopting Linear Regression method, to obtain corrected hyperspectral data, wherein, the hyperspectral data of the plants to be identified are collected by a hyperspectral ground object spectrometer provided within an unmanned aerial vehicle (UAV);

a first processing module, configured to perform external parameter orthogonalisation (EPO) processing for the corrected hyperspectral data, to obtain EPO processed hyperspectral data;

a second processing module, configured to perform first order differential processing for the EPO processed hyperspectral data, to obtain hyperspectral data highlighting the absorption peak information;

a transformation module, configured to perform discrete wavelet transformation processing for the hyperspectral data highlighting the absorption peak information by adopting discrete wavelet transformation, to obtain wavelet coefficients corresponding to the plants to be identified;

a third processing module, configured to obtain a set of physiological characteristic parameters corresponding to the plants to be identified according to the wavelet coefficients corresponding to the plants to be identified and a preset quantitative inversion model, wherein the set of physiological characteristic parameters includes at least one physiological characteristic parameter; and a first determining module, configured to determine plant species corresponding to the set of physiological characteristic parameters according to a preset plant database, wherein the plant database includes a set of physiological characteristic parameters corresponding to different plant species.

Further, the correction module is specifically configured to:

determine the corrected hyperspectral data according to the hyperspectral data, i.e. $DN=k*R+b$, wherein R is the hyperspectral data, and k and b are constant coefficients respectively.

Further, the first processing module includes:

a first determining submodule, configured to determine a projection matrix P according to a spectral matrix, i.e. $X=XP+XQ+R$, wherein X is a matrix of the corrected hyperspectral data, P is a projection matrix for information that is useful for data prediction in the corrected hyperspectral data, Q is a projection matrix for information that is useless for data prediction in the corrected hyperspectral data, and R is a preset residual matrix; and a second determining submodule, configured to determine a orthogonalisation matrix according to the matrix X of the corrected hyperspectral data and the projection matrix P, i.e. $X^*=XP$, and determine that the orthogonalisation matrix $X^*$ is the EPO processed hyperspectral data.

Further, the controller further includes:

a fourth processing module, configured to preprocess the hyperspectral data of plants to be studied, to obtain wavelet coefficients corresponding to the plants to be studied before the third processing module obtains the set of physiological characteristic parameters corresponding to the plants to be studied according to the wavelet coefficients corresponding to the plants to be studied and a preset quantitative inversion model, wherein the plants to be studied are plants of known plant species; and a second determining module, configured to perform multiple regression fitting processing using the wavelet coefficients corresponding to the plants to be studied as independent variables, and the set of physiological characteristic parameters corresponding to the plants to be studied, obtained through the biochemistry experiments as dependent variables, to obtain the quantitative inversion model.

Further, the fourth processing module is specifically configured to:

perform atmospheric radiation correction for the hyperspectral data of plants to be studied by adopting Linear Regression method, to obtain corrected hyperspectral data of plants to be studied;

perform EPO processing for the corrected hyperspectral data of the plants to be studied, to obtain EPO processed hyperspectral data of the plants to be studied;

perform first order differential processing for the EPO processed hyperspectral data of the plants to be studied, to obtain hyperspectral data of the plants to be studied highlighting the absorption peak information; and perform discrete wavelet transform processing for the hyperspectral data of the plants to be studied highlighting the absorption peak information by adopting discrete wavelet transformation, to obtain wavelet coefficients corresponding to the plants to be studied.

Further, the system further includes:

the UAV, the hyperspectral ground object spectrometer and the attitude and position measuring device; wherein the attitude and position measuring device is arranged within the UAV, and the controller is electrically connected to the hyperspectral ground object spectrometer and the attitude and position measuring device respectively;

the attitude and position measuring device is configured to receive a first trigger instruction sent by the controller, and conduct navigation and positioning of the UAV according to the first trigger instruction, such that the UAV arrives at a preset locating position;

the controller is further configured to send the collecting instruction to the hyperspectral ground object spectrometer after determining that the UAV has arrived at the preset locating position;

the hyperspectral ground object spectrometer is configured to receive the collecting instruction sent by the controller, and collect the hyperspectral data according to the collecting instruction.

Further, a gyroscope stable platform is fixedly arranged within the UAV;

the hyperspectral ground object spectrometer is fixedly connected with the gyroscope stable platform through the clamping mechanism.

Further, a buffer layer is fixedly arranged within the UAV;

a bolt hole plate is arranged on the buffer layer, and the gyroscope stable platform is fixedly connected with the bolt hole plate through the fastening bolt.

Further, the UAV further includes a data storage device, wherein, the data storage device includes a processor and dual SD card, and the processor is electrically connected with the dual SD card;

the controller is electrically connected with the processor, the processor is electrically connected with the attitude and position measuring device, and the dual SD card is electrically connected with the hyperspectral ground object spectrometer;

the data storage device is configured to receive a second trigger instruction sent by the controller, generate the collecting instruction according to the second trigger instruction, and send the collecting instruction to the hyperspectral ground object spectrometer;

the hyperspectral ground object spectrometer is configured to collect hyperspectral data of the plants to be identified and information of the hyperspectral ground object spectrometer according to the collecting instruction, and send the hyperspectral data of the plants to be identified and the information of the hyperspectral ground object spectrometer to the data storage device, such that the data storage device stores the hyperspectral data of the plants to be identified and the information of the hyperspectral ground object spectrometer.

Further, the hyperspectral ground object spectrometer is further configured to collect the hyperspectral data of black-and-white board on the ground;

the data storage device is further configured to rectify the hyperspectral data of the plants to be identified according to the hyperspectral data of the black-and-white board on the ground.

Further, the system further includes a power supply equipment; wherein the power supply equipment includes a battery and a power supply circuit, and the battery is electrically connected to the hyperspectral ground object spectrometer, the controller and the data storage device separately through the power supply circuit, and the battery is configured to supply power for the hyperspectral ground object spectrometer, the controller, and the data storage device.

The technical effect of the disclosure is as follows: performing atmospheric radiation correction for the hyperspectral data of plants to be identified adopting Linear Regression method, to obtain corrected hyperspectral data; performing external parameter orthogonalisation (EPO) processing for the corrected hyperspectral data, to obtain EPO processed hyperspectral data; performing first order differential processing for the EPO processed hyperspectral data, to obtain hyperspectral data highlighting absorption peak information; performing discrete wavelet transformation processing for the hyperspectral data highlighting the absorption peak information by adopting discrete wavelet transformation, to obtain wavelet coefficients corresponding to the plants to be identified; obtaining a set of physiological characteristic parameters corresponding to the plants to be identified according to the wavelet coefficients corresponding to the plants to be identified and a preset quantitative inversion model, wherein the set of physiological characteristic parameters includes at least one physiological characteristic parameter; determining plant species corresponding to the set of physiological characteristic parameters according to a preset plant database, wherein the plant database includes a set of physiological characteristic parameters corresponding to different plant species. Thus, a method for identifying plant species based on hyperspectral data is provided, which can be used to analyze hyperspectral data of plants to be identified, to obtain corresponding wavelet coefficients corresponding to the plants to be identified; then the wavelet coefficients corresponding to the plant to be identified can be substituted into the quantitative inversion model, to obtain the set of physiological characteristic parameters corresponding to plants to be identified; and the information of plant species corresponding to the set of physiological characteristic parameters can be queried in the plant database. Thus, the plant species is no longer determined merely by the biochemical experiment method, and the plant species can also be quickly determined by the method provided in the present embodiments.

BRIEF DESCRIPTION OF THE DRAWINGS

FIG. 1 is a flowchart of a method for identifying plant species based on hyperspectral data provided in embodiment 1 of the present disclosure.

FIG. 2 is a flowchart of a method for identifying plant species based on hyperspectral data provided in embodiment 2 of the present disclosure.

DETAILED DESCRIPTION

In order to make the objective, the technical scheme and the advantages of the embodiments of the disclosure more clear, the technical scheme in the embodiments of the disclosure is clearly and completely described below with reference to accompanying drawings in the embodiments of the disclosure. It is clear that the described embodiments are only a part of the embodiments of the disclosure, rather than all of the embodiments. Based on the embodiments of the disclosure, all other embodiments obtained by those of ordinary skill in the art without creative labor are in the scope of the protection of the disclosure.

The way of obtaining information for plant species using biochemical measuring method needs long time experimental analysis, thus the efficiency for analysis is low. With the rapid development of hyperspectral remote sensing technology and the continuous improvement of data processing and analysis methods, highspectral data of plants can be collected and analyzed; at present, using hyperspectral data to identify and analyze plant species is still a technical problem that needs to be improved.

The present disclosure provides a method and system for identifying plant species based on hyperspectral data, which aims to solve the above technical problems existed in the prior art.

The technical scheme of the disclosure and the content on how the technical scheme of this application solves the above technical problems are described below in detail with reference to specific embodiments. The following specific embodiments can be combined with each other, and the same or similar concepts or processes may not be repeated in some embodiments. The embodiments of the present disclosure will be described below in combination with the accompanying drawings.

FIG. 1 is a flowchart of a method for identifying plant species based on hyperspectral data provided in embodiment 1 of the present disclosure, as shown in FIG. 1, the method of the present embodiment includes:

step 101: performing by a controller atmospheric radiation correction for the hyperspectral data of plants to be identified by adopting Linear Regression method, to obtain corrected hyperspectral data, wherein, the hyperspectral data of the plants to be identified are collected by the hyperspectral ground object spectrometer provided within an UAV.

Optionally, the step 101 specifically includes: determining by the controller the corrected hyperspectral data according to the hyperspectral data, i.e. $DN=k*R+b$, wherein R is the hyperspectral data, and k and b are constant coefficients respectively.

In the present embodiment, specifically, for the plants to be identified, the hyperspectral ground object spectrometer can be first used to collect hyperspectral data of plants to be identified. Specifically, the hyperspectral ground object spectrometer is provided within the UAV, and the hyperspectral ground object spectrometer is carried by the UAV to the sampling area, then the hyperspectral ground object spectrometer is used to collect the hyperspectral data of the plants to be identified.

Then Linear Regression method is used to perform atmospheric radiation correction for the hyperspectral data of the plants to be identified. Specifically, for hyperspectral data, since the hyperspectral curve of plants is essentially the reflectivity of plants to different wavelengths, thus the measured hyperspectral data of plants refer to reflectivity, and the reflectivity is also called as reflection spectrum. A correlation between reflection spectrum and atmospheric radiation spectrum is established by using linear regression. After calculating the coefficients k, b, the formula $DN=k*R+b$ is obtained, wherein, k and b are constant coefficients respectively, R is the highspectral data of plants to be identified, DN is the corrected hyperspectral data, and then the corrected hyperspectral data of the plants to be identified are calculated.

Step 102: performing by the controller external parameter orthogonalisation (EPO) processing for the corrected hyperspectral data, to obtain EPO processed hyperspectral data.

Optionally, the step 102 specifically includes:

determining by the controller a projection matrix P according to a spectral matrix, i.e. $X=XP+XQ+R$, wherein, X is a matrix of the corrected hyperspectral data, P is a projection matrix for information that is useful for data prediction in corrected hyperspectral data, Q is a projection matrix for information that is useless for data prediction in corrected hyperspectral data, and R is a preset residual matrix; and determining by the controller a orthogonalisation matrix according to the matrix X of the corrected hyperspectral data and the projection matrix P, i.e. $X^*=XP$, and determining that the orthogonalisation matrix $X^*$ is the EPO processed hyperspectral data.

In the present embodiment, specifically, EPO processing is performed for the corrected hyperspectral data of plants to be identified, to obtain EPO processed hyperspectral data.

Specifically, when the plant type is inverted, the soil moisture of the ground surface is an important disadvantage factor affecting the accuracy of plant inversion model. Therefore, the EPO method is needed to reduce the influence of soil moisture when hyperspectral data of plants is analyzed to obtain plant type. First, the projection matrix P is determined according to the spectral matrix, $X=XP+XQ+R$, wherein, X is a matrix of the corrected hyperspectral data, P is a projection matrix for information that is useless for data prediction in corrected hyperspectral data, and R is a preset residual matrix; then the EPO processed hyperspectral data is determined according to the matrix X of the corrected hyperspectral data and the projection matrix P, i.e. $X^*=XP$.

Step 103: performing by the controller first order differential processing for the EPO processed hyperspectral data, to obtain hyperspectral data highlighting an absorption peak information.

In the present embodiment, specifically, the controller performs first order differential processing for the EPO processed hyperspectral data to highlight the absorption peak of the spectrum, to obtain the hyperspectral data of plants to be identified highlighting an absorption peak information.

Step 104: performing by the controller discrete wavelet transformation processing for the hyperspectral data highlighting the absorption peak information by adopting discrete wavelet transformation, to obtain wavelet coefficients corresponding to the plants to be identified.

In the present embodiment, specifically, the controller performs discrete wavelet transformation processing for the hyperspectral data highlighting the absorption peak information by adopting discrete wavelet transformation; and then for the plants to be identified, the high frequency coefficient and low frequency coefficient for the plants to be identified are obtained. The high frequency coefficients and low frequency coefficients are wavelet coefficients corresponding to the plants to be identified.

Step 105: obtaining by the controller a set of physiological characteristic parameters corresponding to the plants to be identified according to the wavelet coefficients of the plants to be identified and a preset quantitative inversion model, wherein the set of physiological characteristic parameters includes at least one physiological characteristic parameter.

In the present embodiment, specifically, a quantitative inversion model has been set up in advance, and the quantitative inversion model characterizes the characteristics of different species of plants. The wavelet coefficients corresponding to the plant to be identified can be substituted into the quantitative inversion model, to obtain the set of physiological characteristic parameters corresponding to plants to be identified, wherein the set of physiological characteristic parameters includes at least one physiological parameters. For example, the set of physiological characteristic parameters includes chlorophyll content of the plant to be identified, moisture content of the plant to be identified, carotene content of the plant to be identified, nitrogen content of the plant to be identified, cellulose content of the plant to be identified and xylogen content of the plant to be identified.

Step 106: determining by the controller plant species corresponding to the set of physiological characteristic parameters according to a preset plant database, wherein the plant database includes a set of physiological characteristic parameters corresponding to different plant species.

In the present embodiment, specifically, a plant database is set up first. Specifically, plants are collected by UAV in sampling area. For example, a 30 m*30 m quadrat is used, to collect all species inside. Then the plants in the sampling area are classified, and three level, i.e., the families, genera and species of the plants are recorded, then the class of plant species of each plant is determined. Then the physiological characteristic parameters of the plants in the sampling area are determined by indoor biochemical determination method, and then the set of physiological characteristic parameters of each plant species in the sampling area is obtained. Similarly, the set of physiological characteristic parameters of each plant species includes at least one physiological characteristic parameter. For example, the set of physiological characteristic parameters of each plant species includes chlorophyll content, moisture content, carotene content, nitrogen content, cellulose content and xylogen content of leaves, etc. And then, a plant database is established based on each plant species and the set of physiological characteristic parameters of each plant species.

Query is performed in the above plant database according to the set of physiological characteristic parameters corresponding to the plants to be identified, to obtain the set of physiological characteristic parameters corresponding to the plant to be identified. Then, the information of plant species corresponding to the set of physiological characteristic parameters can be determined.

In the present embodiment, performing by a controller atmospheric radiation correction for the hyperspectral data of plants to be identified adopting Linear Regression method, to obtain corrected hyperspectral data, wherein, the hyperspectral data of the plants to be identified are collected by a hyperspectral ground object spectrometer provided within an unmanned aerial vehicle (UAV); performing by the controller external parameter orthogonalisation (EPO) processing for the corrected hyperspectral data, to obtain EPO processed hyperspectral data; performing by the controller first order differential processing for the EPO processed hyperspectral data, to obtain hyperspectral data highlighting absorption peak information; performing by the controller discrete wavelet transformation processing for the hyperspectral data highlighting the absorption peak information by adopting discrete wavelet transformation, to obtain wavelet coefficients corresponding to the plants to be identified; obtaining by the controller a set of physiological characteristic parameters corresponding to the plants to be identified according to the wavelet coefficients corresponding to the plants to be identified and a preset quantitative inversion model, wherein the set of physiological characteristic parameters includes at least one physiological characteristic parameter; determining by the controller plant species corresponding to the set of physiological characteristic parameters according to a preset plant database, wherein the plant database includes a set of physiological characteristic parameters corresponding to different plant species. Thus, a method for identifying plant species based on hyperspectral data is provided, which can be used to analyze hyperspectral data of plants to be identified, to obtain wavelet coefficients corresponding to the plants to be identified; then the wavelet coefficients corresponding to the plant to be identified can be substituted into the quantitative inversion model, to obtain the set of physiological characteristic parameters corresponding to plants to be identified; and the information of plant species corresponding to the set of physiological characteristic parameters can be queried in the plant database. Thus, the plant species is no longer determined merely by the biochemical experiment method, and the plant species can also be quickly determined by the method provided in the present embodiments. Moreover, the hyperspectral ground object spectrometer is carried by UAV to the sampling area to collect the hyperspectral data, which is convenient for data collection, has low cost, small risk, and can test and monitor the same area repeatedly in the short period.

FIG. 2 is a flowchart of a method for identifying plant species based on hyperspectral data provided in embodiment 2 of the present disclosure. As shown in FIG. 2, the method of the present embodiment includes:

step 201: preprocessing by the controller hyperspectral data of plants to be studied, to obtain wavelet coefficients corresponding to the plants to be studied, wherein the plants to be studied are plants of known plant species.

In an optional implementation, step 201 specifically includes the following steps:

performing by the controller atmospheric radiation correction for the hyperspectral data of plants to be studied by adopting Linear Regression method, to obtain corrected hyperspectral data of plants to be studied;

performing by the controller EPO processing for the corrected hyperspectral data of the plants to be studied, to obtain EPO processed hyperspectral data of the plants to be studied;

performing by the controller first order differential processing for the EPO processed hyperspectral data of the plants to be studied, to obtain hyperspectral data of the plants to be studied highlighting the absorption peak information; and performing by the controller discrete wavelet transform processing for the hyperspectral data of the plants to be studied highlighting the absorption peak information by adopting discrete wavelet transformation, to obtain wavelet coefficients corresponding to the plants to be studied.

In the present embodiment, specifically, first it is needed to use hyperspectral ground object spectrometer to sample the plants in the study area, to collect the hyperspectral data of the plants. The sampling can be carried out by adopting UAV with the hyperspectral ground object spectrometer. First, the sampling needs to be carried out in a sunny day to ensure that the hyperspectral data of the plants will be collected when the light intensity meets the requirements of the measurement. For example, the sampling time can be set at about 5 hours before the strongest sunshine and 5 hours after the strongest sunshine in the study area, 10 spectra are collected each time, and the absorption band is 400 nm-1100 nm. A suitable number of survey quadrats can be set up in the study area. For example, the survey quadrat is 30 m*30 m. Then based on the vegetation distribution in the study area, the hyperspectral data of the main species are collected in the study area. The hyperspectral data obtained here are the hyperspectral data of the plants to be studied.

Because the reflection data received by the hyperspectral ground object spectrometer mainly come from ground diffuse reflection and atmospheric radiation, and atmospheric radiation will interfere with the hyperspectral data of plants collected by the hyperspectral ground object spectrometer, so the atmospheric radiation is an error term. The Linear Regression method can be used to remove the interference on the hyperspectral data of plants caused by atmospheric radiation.

The measured hyperspectral data of plants refers to reflectivity, and the reflectivity is also called as reflection spectrum. The spectral values of ground reflection of two calibration points are measured, and the average spectral values of atmospheric radiation for corresponding pixels on the image are calculated. A correlation between reflection spectrum and atmospheric radiation spectrum is established by using linear regression. After calculating the coefficients k, b, the formula $DN=k*R+b$ is obtained, wherein, k and b are constant coefficients respectively, R is the highspectral data of plants to be identified, DN is the corrected hyperspectral data, and then the corrected hyperspectral data are calculated.

In the process of adopting the Linear Regression method, the requirements for the calibration point are as follow: first, the selection of the calibration point requires uniform ground object as isotropic as possible; the ground object on the calibration point should span as wide spectral range of the earth reflection as possible, and the altitude of the calibration point should be kept the same as the study area as far as possible.

For example, the bare soil area and Hulun Lake on Hulun Buir Grassland can be taken as bright target and dark target to perform atmospheric correction, and the bright target and the dark target here are the calibration points mentioned above. Then, field ground object spectrometer is used to measure the absolute reflectivity for the bright target and the absolute reflectivity for the dark target. The absolute reflectivity of the bright target and the absolute reflectivity for the dark target are used to complete the fitting of the linear regression equation $DN=k*R+b$.

Then, EPO processing is performed for the corrected hyperspectral data of the plants to be studied, to obtain EPO processed hyperspectral data of the plants to be studied. Specifically, the manner of step 102 can be used to perform EPO processing for the corrected hyperspectral data of the plants to be studied.

Then, first order differential processing is performed for the EPO processed hyperspectral data to highlight the absorption peak of the spectrum, and to obtain hyperspectral data highlighting absorption peak information;

Then, discrete wavelet transformation processing is performed for the hyperspectral data highlighting the absorption peak information by adopting discrete wavelet transformation; and then for the plants to be studied, the high frequency coefficient and low frequency coefficient for the plants to be studied are obtained. The high frequency coefficients and low frequency coefficients are wavelet coefficients corresponding to the plants to be studied.

Step 202: performing by the controller multiple regression fitting processing using the wavelet coefficients corresponding to the plants to be studied as independent variables, and the set of physiological characteristic parameters corresponding to the plants to be studied, obtained through the biochemistry experiments as dependent variables, to obtain the quantitative inversion model.

In the present embodiment, specifically, the biochemical determination method can be used to carry out experimental analysis for the plant to be studied, to obtain the set of physiological characteristic parameters of the plants to be studied. Then, the wavelet coefficients corresponding to the plants to be studied are used as independent variables, and the set of physiological characteristic parameters corresponding to the plants to be studied, obtained through the biochemistry experiments are used as dependent variables, to perform multiple regression fitting processing for the above parameters, and thus the quantitative inversion model is obtained.

For example, the wavelet coefficients corresponding to the plants to be studied are used as independent variables, and the chlorophyll content, moisture content, carotene content, nitrogen content, cellulose content and xylogen content are used as the dependent variable, to perform partial least squares regression analysis. Then, a quantitative inversion model is obtained.

Step 203: performing by the controller atmospheric radiation correction for the hyperspectral data of plants to be identified by adopting Linear Regression method, to obtain corrected hyperspectral data, wherein, the hyperspectral data of the plants to be identified are collected by the hyperspectral ground object spectrometer provided within an unmanned aerial vehicle (UAV).

In the present embodiment, specifically, this step may reference to step 101 of FIG. 1, and thus is not detailed any more.

Step 204: performing by the controller EPO processing for the corrected hyperspectral data, to obtain EPO processed hyperspectral data.

In the present embodiment, specifically, this step may reference to step 102 of FIG. 1, and thus is not detailed any more.

Step 205: performing by the controller first order differential processing for the EPO processed hyperspectral data, to obtain hyperspectral data highlighting an absorption peak information.

In the present embodiment, specifically, this step may reference to step 103 of FIG. 1, and thus is not detailed any more.

Step 206: performing by the controller discrete wavelet transformation processing for the hyperspectral data highlighting the absorption peak information by adopting discrete wavelet transformation, to obtain wavelet coefficients corresponding to the plants to be identified.

In the present embodiment, specifically, discrete wavelet transformation processing is performed for the hyperspectral data highlighting the absorption peak information.

Wavelet is local analysis for time frequency. It gradually achieves multi-scale refinement for signal through scaling and translation operations, and finally achieves the effects of time division at high frequency and frequency division at low frequency. It can automatically adapt to the requirements of time-frequency signal analysis, and thus any details of the signal can be focused. There are several kinds of common wavelet functions. The common wavelet functions and their properties are shown in table 1.

TABLE 1

The common wavelet functions and their properties

| Wavelet functions | Haar | Daubechies | Biorthogonal | Coiflets | Symlets | Morlet | Mexican Hat | Meyer |
|---|---|---|---|---|---|---|---|---|
| Abbreviation of wavelet | haar | db | bior | coif | sym | morl | mexh | meyr |
| Form of expression | haar | db N | biorNr.Nd | coif N | sym N | morl | mexh | meyr |
| Illustration | haar | db3 | bior2.4 | coif3 | sym2 | morl | mexh | meyr |
| Orthogonality | have | have | not have | have | have | not have | not have | have |
| Biorthogonality | have | have | have | have | have | not have | not have | have |
| Compactly supported | have | have | have | have | have | not have | not have | not have |
| Continuous wavelet transform | can | can | can | can | can | can | can | can |
| Discrete wavelet transform | can | can | can | can | can | can not | can not | can but have no FWT |
| Support length | 1 | 2N − 1 | Reconstruction: 2Nr + 1 decomposition: 2Nd + 1 | 6N − 1 | 2N − 1 | finite length | finite length | finite length |
| Filter length | 2 | 2N | Max (2Nr, 2Nd) + 2 | 6N | 2N | [−4, 4] | [−5, 5] | [−8, 8] |
| Symmetry | symmetrical | approximately symmetrical | asymmetrical | approximately symmetrical | approximately symmetrical | symmetrical | symmetrical | symmetrical |

Because the amount for the collected hyperspectral data is very large, and there is a serious linear redundancy, so a spectral analysis manner for reducing data dimension and maximally ensuring data information is needed. It can be known through table 1 that the discrete wavelet transformation function is an excellent spectral data analysis manner, which can reserve the local and holistic characteristics of the spectral data to the maximum extent.

Then, after performing the discrete wavelet transformation processing, the wavelet coefficients corresponding to the plants to be identified are obtained.

Step 207: obtaining by the controller the set of physiological characteristic parameters corresponding to the plants to be identified according to the wavelet coefficients of the plants to be identified and a preset quantitative inversion model, wherein the set of physiological characteristic parameters includes at least one physiological characteristic parameter.

In the present embodiment, specifically, this step may reference to step 105 of FIG. 1, and thus is not detailed any more.

Step 208: determining by the controller plant species corresponding to the set of physiological characteristic parameters according to a preset plant database, wherein the plant database includes a set of physiological characteristic parameters corresponding to different plant species.

In the present embodiment, specifically, this step may reference to step 106 of FIG. 1, and thus is not detailed any more.

In the present embodiment, performing by a controller atmospheric radiation correction for the hyperspectral data of plants to be identified adopting Linear Regression method, to obtain corrected hyperspectral data, wherein, the hyperspectral data of the plants to be identified are collected by a hyperspectral ground object spectrometer provided within an unmanned aerial vehicle (UAV); performing by the controller external parameter orthogonalisation (EPO) processing for the corrected hyperspectral data, to obtain EPO processed hyperspectral data; performing by the controller first order differential processing for the EPO processed hyperspectral data, to obtain hyperspectral data highlighting absorption peak information; performing by the controller discrete wavelet transformation processing for the hyperspectral data highlighting the absorption peak information by adopting discrete wavelet transformation, to obtain wavelet coefficients corresponding to the plants to be identified; obtaining by the controller a set of physiological characteristic parameters corresponding to the plants to be identified according to the wavelet coefficients corresponding to the plants to be identified and a preset quantitative inversion model, wherein the set of physiological characteristic parameters includes at least one physiological characteristic parameter; determining by the controller plant species corresponding to the set of physiological characteristic parameters according to a preset plant database, wherein the plant database includes a set of physiological characteristic parameters corresponding to different plant species. Thus, a method for identifying plant species based on hyperspectral data is provided, which can be used to analyze hyperspectral data of plants to be identified, to obtain corresponding wavelet coefficients corresponding to the plants to be identified; then the wavelet coefficients corresponding to the plant to be identified can be substituted into the quantitative inversion model, to obtain the set of physiological characteristic parameters corresponding to plants to be identified; and the information of plant species corresponding to the set of physiological characteristic parameters can be queried in the plant database. Thus, the plant species is no longer determined merely by the biochemical experiment method, and the plant species can also be quickly determined by the method provided in the present embodiments. In addition, by analyzing the hyperspectral data of the plant for which the plant species have been acquired, and obtaining a set of physiological characteristic parameters based on biochemical experiments, the above quantitative inversion model can be established. Moreover, the hyperspectral ground object spectrometer is carried by UAV to the sampling area to collect the hyperspectral data, which is convenient for data collection, has low cost, small risk, and can test and monitor the same area repeatedly in a short period.

On the basis of the embodiments shown in FIG. 2, an attitude and position measuring device is further provided within the UAV. Accordingly, before step 201, the following steps can further be included:

Step 301: receiving by the attitude and position measuring device a first trigger instruction sent by the controller, and performing position navigation for the UAV according to the first trigger instruction, such that the UAV arrive at a preset locating position.

In the present embodiment, specifically, with the development of UAV technology, UAV is set out to be applied to remote sensing technology. Comparing with the traditional satellite remote sensing technology, the remote sensing information obtained by UAV hyperspectral remote sensing technology is advantageous in terms of time scale, spatial resolution and data dimension and so on; wherein, UAV hyperspectral remote sensing technology is a hyperspectral imaging system combining and intercrossing UAV technology and hyperspectral technology deeply, and belongs to a part of aerial spectrum remote sensing detection.

In the present embodiment, the hyperspectral ground object spectrometer and the attitude and position measuring device are arranged within the UAV; the controller and the hyperspectral ground object spectrometer can be electrically connected remotely, and the controller and the attitude and position measuring device can be electrically connected remotely. The controller can be used as a ground monitoring device, to control the flight of UAV and the collection of hyperspectral data. Wherein, a velocity of data collection of hyperspectral ground object spectrometer is about 100 milliseconds/single spectrum. The controller is also called the upper computer.

A gyroscope stable platform is fixedly arranged within the UAV, and the hyperspectral ground object spectrometer is fixedly connected to the gyroscope stable platform through the clamping mechanism. Then the hyperspectral ground object spectrometer is set up in the interior of UAV, and the gyroscope stable platform can ensure that during the flight of UAV, the hyperspectral ground object spectrometer will not subject to a large sloshing. Specifically, a buffer layer is fixedly arranged in the interior of UAV, and a bolt hole plate is arranged on the buffer layer; the gyroscope stable platform can be fixedly connected with the bolt hole plate through the fastening bolt, then the gyroscope stable platform is installed in the interior of UAV. The buffer layer can ensure the stability of the gyroscope stable platform during the flight of UAV, and then the hyperspectral ground object spectrometer is fixedly connected to the gyroscope stable platform through the clamping mechanism.

A data storage device is further provided within the UAV, which consists of a processor and dual secure digital (for short SD) card. The processor is electrically connected to the dual SD card. Control device of the UAV is electrically connected to the processor, and the processor is electrically connected with the attitude and position measuring device. The dual SD card is electrically connected with the hyperspectral ground object spectrometer. A power supply equipment is further provided in the UAV, which consists of a battery and a power supply circuit. The battery is electrically connected through the power supply circuit to the hyperspectral ground object spectrometer, the control device of the UAV and the data storage device respectively, and then the battery can supply power for the hyperspectral ground object spectrometer, the control device of UAV, and the data storage device.

Before the UAV takes off, the above equipment and devices are first installed in the UAV, then such processes like equipment assembly and debugging, flight route planning, overall debugging of flight system, parameters configuration of hyperspectral ground object spectrometer, and collection of dark current and collection of the hyperspectral data of whiteboard are performed. Wherein, dark current and the hyperspectral data of whiteboard are used for ground calibration, and the hyperspectral data of whiteboard is used to calibrate the reflectivity of the ground objects measured by a hyperspectral ground object spectrometer during the flight process. In addition, it is necessary to adjust focus for the hyperspectral ground object spectrometer, and to set up such collecting parameters like spectral channel and integration time for the high spectral ground object spectrometer. It is also necessary to adjust the flight speed of UAV by airborne algorithm, so that the flight speed can match the collecting parameters of the hyperspectral ground object spectrometer. It is necessary to lay down ground air strip to calibrate the black-and-white board. The black-and-white board can effectively correct atmosphere affected components of the collected hyperspectral data of the plants to be identified, which can then be used for the follow-up flight test to collect the hyperspectral data of the black-and-white board on the air strip, and to perform atmospheric correction for the highspectral data of the plants to be identified.

When, after UAV takes off, the controller sends a first control command to the control device of the UAV; and the control device of the UAV sends a first trigger instruction to the attitude and position measuring device through the data storage device. The attitude and position measuring device conducts navigation and positioning of the UAV according to the first trigger instruction, and then controls the UAV to arrive at a preset locating position.

Step 302: sending by the controller the collecting instruction to the hyperspectral ground object spectrometer after determining that the UAV has arrived at a preset locating position.

In an optional embodiment, step 302 includes: sending by the controller a second trigger instruction to the data storage device after determining that the UAV has arrived at the preset locating position; generating by the data storage device collecting instruction according to the second trigger instruction, and sending the collecting instruction to the hyperspectral ground object spectrometer.

In the present embodiment, specifically, after determining by the controller the UAV has arrived at the preset locating position, the data storage device receives the instructions sent by the controller from the control device of the UAV, to collect and store the hyperspectral data of the plants to be identified and the information of the hyperspectral ground object spectrometer according to the set air route. Specifically, after determining the UAV has arrived at the preset locating position, the control device of the UAV sends response information to the controller. Then the controller sends a second control command to the control device of the UAV, and the control device of the UAV sends a trigger signal in a specific format to the data storage device. The trigger signal is a second trigger instruction, and then the data storage device send collecting instruction to the highspectrum ground object spectrometer.

Step 303: collecting by the hyperspectral ground object spectrometer the highspectral data of the plants to be identified according to the collecting instruction.

In an alternative embodiment, step 303 specifically includes: collecting by the highspectrum ground object spectrometer the hyperspectral data of plants to be identified and the information of the highspectrum ground object spectrometer according to the collecting instruction; and sending the hyperspectral data of plants to be identified and the information of the highspectrum ground object spectrometer to the data storage device; storing by the data storage device the hyperspectral data of plants to be identified and the information of the highspectrum ground object spectrometer.

In the present embodiment, specifically, the highspectrum ground object spectrometer initially collects the hyperspectral data of plants to be identified and the information of the highspectrum ground object spectrometer. Then the data storage device can acquire the hyperspectral data of plants to be identified and the information of the highspectrum ground object spectrometer mentioned above and stores them. The information of the highspectrum ground object spectrometer includes geographic position information and attitude parameters of the highspectrum ground object spectrometer. The attitude parameters are used to determine the spatial state and operation state of the hyperspectral ground object spectrometer. For example, the geographic position information of the highspectrum ground object spectrometer includes longitude information, latitude information and altitude information, and the attitude parameters include yawing information, rolling information, pitching information, acceleration and angular velocity.

Step 304: collecting by the hyperspectral ground object spectrometer the hyperspectral data of black-and-white board on the ground.

Step 305: rectifying by the data storage device the hyperspectral data of the plants to be identified according to the hyperspectral data of the black-and-white board on the ground.

In the present embodiment, specifically, the hyperspectral ground object spectrometer further collects the hyperspectral data of black-and-white board on the ground. Then, the data storage device acquires the hyperspectral data of the black-and-white board on the ground, and the data storage device takes the hyperspectral data of the black-and-white board on the ground as a basis for atmospheric correction, to rectify the hyperspectral data of the plant to be identified according to the hyperspectral data of the black-and-white board on the ground.

Then, after all the setting air routes have been tested, the controller sends control instruction to the control device of UAV, then the control device of UAV sends instruction to the data storage device. The data storage device then sends end instruction to the hyperspectral ground object spectrometer, to end the data collection process.

Then, after the flight of UAV is completed, the data storage device and controller are connected through a cable; then, the controller loaded with special acquisition and control software, sends download instruction to the data storage device through specific protocol, to obtain various data and information in the data storage device. The controller can then use geometric correction software to perform the process like geometric correction for the downloaded data. Then, the controller can perform the steps subsequent to the step 201.

Accordingly, the hyperspectral ground object spectrometer can be provide within the UAV, and the same area can be tested and monitored repeatedly in a short period of time. The stability of the hyperspectral ground object spectrometer can be ensured through the gyroscope stable platform during the flight of the UAV. The data storage device can store the collected hyperspectral data and the information of the hyperspectral ground object spectrometer, and can store more data and information. Moreover, the flight speed of the UAV matches the collection speed of the hyperspectral ground object spectrometer, the storage speed of the data storage device, which facilitates the subsequent processing of hyperspectral data and image correction.

Figure 3:
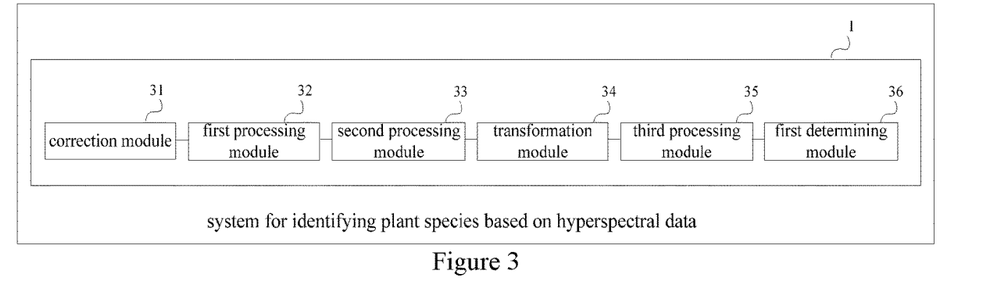
FIG. 3 is a structural schematic diagram of a system for identifying plant species based on hyperspectral data provided in embodiment 3 of the present disclosure.

FIG. 3 is a structural schematic diagram of a system for identifying plant species based on hyperspectral data provided in embodiment 3 of the present disclosure. As shown in FIG. 3, the system provided in the present embodiment includes: a controller 1;

the controller 1 includes:

a correction module 31, configured to perform atmospheric radiation correction for the hyperspectral data of plants to be identified adopting Linear Regression method, to obtain corrected hyperspectral data, wherein, the hyperspectral data of the plants to be identified are collected by a hyperspectral ground object spectrometer provided within an unmanned aerial vehicle (UAV);

a first processing module 32, configured to perform external parameter orthogonalisation (EPO) processing for the corrected hyperspectral data, to obtain EPO processed hyperspectral data;

a second processing module 33, configured to perform first order differential processing for the EPO processed hyperspectral data, to obtain hyperspectral data highlighting the absorption peak information;

a transformation module 34, configured to perform discrete wavelet transformation processing for the hyperspectral data highlighting the absorption peak information by adopting discrete wavelet transformation, to obtain wavelet coefficients corresponding to the plants to be identified;

a third processing module 35, configured to obtain a set of physiological characteristic parameters corresponding to the plants to be identified according to the wavelet coefficients corresponding to the plants to be identified and a preset quantitative inversion model, wherein the set of physiological characteristic parameters includes at least one physiological characteristic parameter; and a first determining module 36, configured to determine plant species corresponding to the set of physiological characteristic parameters according to a preset plant database, wherein the plant database includes a set of physiological characteristic parameters corresponding to different plant species.

Details of the system for identifying plant species based on hyperspectral data provided in this embodiment can be seen with reference to the method for identifying plant species based on hyperspectral data provided in embodiment 1, which is no longer detailed any more.

In the present embodiment, performing atmospheric radiation correction for the hyperspectral data of plants to be identified adopting Linear Regression method, to obtain corrected hyperspectral data, wherein, the hyperspectral data of the plants to be identified are collected by a hyperspectral ground object spectrometer provided within an unmanned aerial vehicle (UAV); performing external parameter orthogonalisation (EPO) processing for the corrected hyperspectral data, to obtain EPO processed hyperspectral data; performing first order differential processing for the EPO processed hyperspectral data, to obtain hyperspectral data highlighting absorption peak information; performing discrete wavelet transformation processing for the hyperspectral data highlighting the absorption peak information by adopting discrete wavelet transformation, to obtain wavelet coefficients corresponding to the plants to be identified; obtaining a set of physiological characteristic parameters corresponding to the plants to be identified according to the wavelet coefficients corresponding to the plants to be identified and a preset quantitative inversion model, wherein the set of physiological characteristic parameters includes at least one physiological characteristic parameter; determining plant species corresponding to the set of physiological characteristic parameters according to a preset plant database, wherein the plant database includes a set of physiological characteristic parameters corresponding to different plant species. Thus, a method for identifying plant species based on hyperspectral data is provided, which can be used to analyze hyperspectral data of plants to be identified, to obtain corresponding wavelet coefficients corresponding to the plants to be identified; then the wavelet coefficients corresponding to the plant to be identified can be substituted into the quantitative inversion model, to obtain the set of physiological characteristic parameters corresponding to plants to be identified; and the information of plant species corresponding to the set of physiological characteristic parameters can be queried in the plant database. Thus, the plant species is no longer determined merely by the biochemical experiment method, and the plant species can also be quickly determined by the method provided in the present embodiments. Moreover, the hyperspectral ground object spectrometer is carried by UAV to the sampling area to collect the hyperspectral data, which is convenient for data collection, has low cost, small risk, and can test and monitor the same area repeatedly in the short period.

Figure 4:
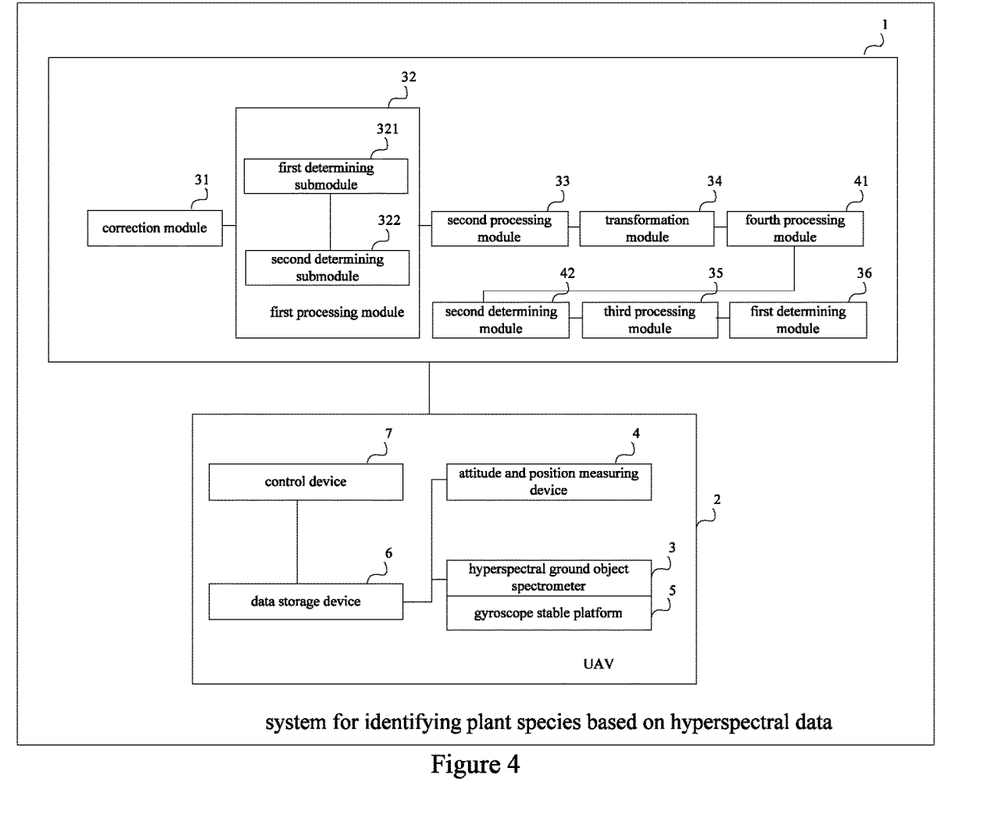
FIG. 4 is a structural schematic diagram of a system for identifying plant species based on hyperspectral data provided in embodiment 4 of the present disclosure.

FIG. 4 is a structural schematic diagram of a system for identifying plant species based on hyperspectral data provided in embodiment 4 of the present disclosure. On the basis of the embodiment shown in FIG. 3, as shown in FIG. 4, a correction module 31 is configured to determine the corrected hyperspectral data according to the hyperspectral data, i.e. DN=k*R+b, wherein R is the hyperspectral data, and k and b are constant coefficients respectively.

A first processing module 32 includes:

a first determining submodule 321, configured to determine a projection matrix P according to a spectral matrix, i.e. X=XP+XQ+R, wherein X is a matrix of the corrected hyperspectral data, P is a projection matrix for information that is useful for data prediction in the corrected hyperspectral data, Q is a projection matrix for information that is useless for data prediction in the corrected hyperspectral data, and R is a preset residual matrix; and a second determining submodule 322, configured to determine a orthogonalisation matrix according to the matrix X of the corrected hyperspectral data and the projection matrix P, i.e. X*=XP, and determine that the orthogonalisation matrix X* is the EPO processed hyperspectral data.

The controller 1 further includes:

a fourth processing module 41, configured to preprocess the hyperspectral data of plants to be studied, to obtain wavelet coefficients corresponding to the plants to be studied before the third processing module 35 obtains the set of physiological characteristic parameters corresponding to the plants to be studied according to the wavelet coefficients corresponding to the plants to be studied and a preset quantitative inversion model, wherein the plants to be studied are plants of known plant species; and a second determining module 42, configured to perform multiple regression fitting processing using the wavelet coefficients corresponding to the plants to be studied as independent variables, and the set of physiological characteristic parameters corresponding to the plants to be studied, obtained through the biochemistry experiments as dependent variables, to obtain the quantitative inversion model.

The fourth processing module 41 is specifically configured to:

perform atmospheric radiation correction for the hyperspectral data of plants to be studied by adopting Linear Regression method, to obtain corrected hyperspectral data of plants to be studied;

perform EPO processing for the corrected hyperspectral data of the plants to be studied, to obtain EPO processed hyperspectral data of the plants to be studied;

perform first order differential processing for the EPO processed hyperspectral data of the plants to be studied, to obtain hyperspectral data of the plants to be studied highlighting the absorption peak information; and perform discrete wavelet transform processing for the hyperspectral data of the plants to be studied highlighting the absorption peak information by adopting discrete wavelet transformation, to obtain wavelet coefficients corresponding to the plants to be studied.

The system for identifying plant species based on hyperspectral data provided in this embodiment further includes: a UAV 2, a hyperspectral ground object spectrometer 3 and an attitude and position measuring device 4; wherein the attitude and position measuring device 4 is provided within the UAV 2, and the controller 1 is electrically connected to the hyperspectral ground object spectrometer 3 and the attitude and position measuring device 4 respectively.

The attitude and position measuring device 4 is configured to receive a first trigger instruction sent by the controller 1, and conduct navigation and positioning of the UAV 2 according to the first trigger instruction, such that the UAV 2 arrives at a preset locating position.

The controller 1 is further configured to send the collecting instruction to the hyperspectral ground object spectrometer 3 after determining that the UAV 2 has arrived at the preset locating position.

The hyperspectral ground object spectrometer 3 is configured to receive the collecting instruction sent by the controller 1, and collect the hyperspectral data according to the collecting instruction.

A gyroscope stable platform 5 is fixedly arranged within the UAV 2, and the hyperspectral ground object spectrometer 3 is fixedly connected to the gyroscope stable platform 5 through the clamping mechanism.

A buffer layer is fixedly arranged within the UAV 2; a bolt hole plate is arranged on the buffer layer, and the gyroscope stable platform 5 is fixedly connected with the bolt hole plate through the fastening bolt.

The UAV 2 further includes a data storage device 6 and a control device 7, wherein, the data storage device 6 includes a processor and dual SD card, and the processor is electrically connected with the dual SD card; the control device 7 is electrically connected with the processor, the processor is electrically connected with the attitude and position measuring device 4, and the dual SD card is electrically connected with the hyperspectral ground object spectrometer 3.

The data storage device 6 is configured to receive a second trigger instruction sent by the controller 1, generate the collecting instruction according to the second trigger instruction, and send the collecting instruction to the hyperspectral ground object spectrometer 3.

The hyperspectral ground object spectrometer 3 is configured to collect hyperspectral data of the plants to be identified and information of the hyperspectral ground object spectrometer 3 according to the collecting instruction, and send the hyperspectral data of the plants to be identified and the information of the hyperspectral ground object spectrometer 3 to the data storage device 6, such that the data storage device 6 stores the hyperspectral data of the plants to be identified and the information of the hyperspectral ground object spectrometer 3.

The hyperspectral ground object spectrometer 3 is further configured to collect the hyperspectral data of black-and-white board on the ground; and the data storage device 6 is further configured to rectify the hyperspectral data of the plants to be identified according to the hyperspectral data of the black-and-white board on the ground.

The system for identifying plant species based on hyperspectral data provided in this embodiment further includes a power supply equipment; wherein the power supply equipment includes a battery and a power supply circuit, and the battery is electrically connected to the hyperspectral ground object spectrometer 3, the control device of UAV 7 and the data storage device 6 separately through the power supply circuit, and the battery is configured to supply power for the hyperspectral ground object spectrometer 3, the control device 7, and the data storage device 6.

Details of the system for identifying plant species based on hyperspectral data provided in this embodiment can be seen with reference to the method for identifying plant species based on hyperspectral data provided in embodiment 2, which is not detailed any more.

In the present embodiment, performing by a controller atmospheric radiation correction for the hyperspectral data of plants to be identified adopting Linear Regression method, to obtain corrected hyperspectral data, wherein, the hyperspectral data of the plants to be identified are collected by a hyperspectral ground object spectrometer provided within an unmanned aerial vehicle (UAV); performing by the controller external parameter orthogonalisation (EPO) processing for the corrected hyperspectral data, to obtain EPO processed hyperspectral data; performing by the controller first order differential processing for the EPO processed hyperspectral data, to obtain hyperspectral data highlighting absorption peak information; performing by the controller discrete wavelet transformation processing for the hyperspectral data highlighting the absorption peak information by adopting discrete wavelet transformation, to obtain wavelet coefficients corresponding to the plants to be identified; obtaining by the controller a set of physiological characteristic parameters corresponding to the plants to be identified according to the wavelet coefficients corresponding to the plants to be identified and a preset quantitative inversion model, wherein the set of physiological characteristic parameters includes at least one physiological characteristic parameter; determining by the controller plant species corresponding to the set of physiological characteristic parameters according to a preset plant database, wherein the plant database includes a set of physiological characteristic parameters corresponding to different plant species. Thus, a method for identifying plant species based on hyperspectral data is provided, which can be used to analyze hyperspectral data of plants to be identified, to obtain corresponding wavelet coefficients corresponding to the plants to be identified; then the wavelet coefficients corresponding to the plant to be identified can be substituted into the quantitative inversion model, to obtain the set of physiological characteristic parameters corresponding to plants to be identified; and the information of plant species corresponding to the set of physiological characteristic parameters can be queried in the plant database. Thus, the plant species is no longer determined merely by the biochemical experiment method, and the plant species can also be quickly determined by the method provided in the present embodiments. In addition, by analyzing the hyperspectral data of plants that the plant species have been known, and obtaining a set of physiological characteristic parameters based on biochemical experiments, the above quantitative inversion models can be established. Moreover, the hyperspectral ground object spectrometer is carried by UAV to the sampling area to collect the hyperspectral data, which is convenient for data collection, has low cost, small risk, and can test and monitor the same area repeatedly in the short period.

It can be understood by those of ordinary skill in the art that all or a part of the steps of implementing the above methods of the embodiments can be accomplished by the relevant hardware instructed by the program. The aforesaid program can be stored in a computer readable storage medium. The program executes the steps of implementing the above methods of the embodiments when executed, and the aforesaid storage media includes various media such as ROM, RAM, disk or CD, which can store program code.

Finally, it should be appreciated that the above embodiments are used only to illustrate the technical scheme of the disclosure in a non limiting manner. Although the present disclosure is explained in detail with reference to the aforesaid embodiments, it should be understood by those of ordinary skill in the art that the technical scheme described by the aforesaid embodiments can still be modified, or some of the technical feature can be replaced equivalently; and these modifications or replacements do not make the essence of the corresponding technical scheme deviate from the spirit and scope of the technical schemes of the present disclosure.

We claim:

1. A method for identifying plant species based on hyperspectral data, comprising:

performing by a controller atmospheric radiation correction for the hyperspectral data of plants to be identified adopting Linear Regression method, to obtain corrected hyperspectral data, wherein, the hyperspectral data of the plants to be identified are collected by a hyperspectral ground object spectrometer provided within an unmanned aerial vehicle (UAV);

performing by the controller external parameter orthogonalisation (EPO) processing for the corrected hyperspectral data, to obtain EPO processed hyperspectral data;

performing by the controller first order differential processing for the EPO processed hyperspectral data, to obtain hyperspectral data highlighting absorption peak information;

performing by the controller discrete wavelet transformation processing for the hyperspectral data highlighting the absorption peak information by adopting discrete wavelet transformation, to obtain wavelet coefficients corresponding to the plants to be identified;

obtaining by the controller a set of physiological characteristic parameters corresponding to the plants to be identified according to the wavelet coefficients corresponding to the plants to be identified and a preset quantitative inversion model, wherein the set of physiological characteristic parameters includes at least one physiological characteristic parameter; and determining by the controller plant species corresponding to the set of physiological characteristic parameters according to a preset plant database, wherein the plant database includes a set of physiological characteristic parameters corresponding to different plant species;

wherein before the controller obtains the set of physiological characteristic parameters corresponding to the plants to be identified according to the wavelet coefficients corresponding to the plants to be identified and the preset quantitative inversion model, further comprising:

preprocessing by the controller the hyperspectral data of plants to be studied, to obtain wavelet coefficients corresponding to the pants to be studied, wherein the plants to be studied are plants of known plant species; and performing by the controller multiple regression fitting processing using the wavelet coefficients corresponding to the plants to be studied as independent variables, and the set of physiological characteristic parameters corresponding to the plants to be studied, obtained through the biochemistry experiments as dependent variables, to obtain the quantitative inversion model.

2. The method according to claim 1, wherein, performing by the controller atmospheric radiation correction for the hyperspectral data of plants to be identified adopting Linear Regression method, to obtain corrected hyperspectral data comprises:

determining by the controller the corrected hyperspectral data according to the hyperspectral data, i.e. $DN=k*R+b$, wherein R is the hyperspectral data, and k and b are constant coefficients respectively.

3. The method according to claim 1, wherein, performing by the controller EPO processing for the corrected hyperspectral data, to obtain EPO processed hyperspectral data comprises:

determining by the controller a projection matrix P according to a spectral matrix, i.e. $X=XP+XQ+R$, wherein, X is a matrix of the corrected hyperspectral data, P is a projection matrix for information that is useful for data prediction in the corrected hyperspectral data, Q is a projection matrix for information that is useless for data prediction in the corrected hyperspectral data, and R is a preset residual matrix; and determining by the controller a orthogonalisation matrix according to the matrix X of the corrected hyperspectral data and the projection matrix P, i.e. $X^*=XP$, and determining that the orthogonalisation matrix $X^*$ is the EPO processed hyperspectral data.

4. The method according to claim 1, wherein, preprocessing by the controller the hyperspectral data of plants to be studied, to obtain wavelet coefficients corresponding to the plants to be studied comprises:

performing by the controller atmospheric radiation correction for the hyperspectral data of plants to be studied by adopting Linear Regression method, to obtain corrected hyperspectral data of plants to be studied;

performing by the controller EPO processing for the corrected hyperspectral data of the plants to be studied, to obtain EPO processed hyperspectral data of the plants to be studied;

performing by the controller first order differential processing for the EPO processed hyperspectral data of the plants to be studied, to obtain hyperspectral data of the plants to be studied highlighting the absorption peak information; and performing by the controller discrete wavelet transform processing for the hyperspectral data of the plants to be studied highlighting the absorption peak information by adopting discrete wavelet transformation, to obtain wavelet coefficients corresponding to the plants to be studied.

5. A system for identifying plant species based on hyperspectral data, comprising a controller; wherein, the controller comprises:

a correction module, configured to perform atmospheric radiation correction for the hyperspectral data of plants to be identified adopting Linear Regression method, to obtain corrected hyperspectral data, wherein, the hyperspectral data of the plants to be identified are collected by a hyperspectral ground object spectrometer provided within an unmanned aerial vehicle (UAV);

a first processing module, configured to perform external parameter orthogonalisation (EPO) processing for the corrected hyperspectral data, to obtain EPO processed hyperspectral data;

a second processing module, configured to perform first order differential processing for the EPO processed hyperspectral data, to obtain hyperspectral data highlighting the absorption peak information;

a transformation module, configured to perform discrete wavelet transformation processing for the hyperspectral data highlighting the absorption peak information by adopting discrete wavelet transformation, to obtain wavelet coefficients corresponding to the plants to be identified;

a third processing module, configured to obtain a set of physiological characteristic parameters corresponding to the plants to be identified according to the wavelet coefficients corresponding to the plants to be identified and a preset quantitative inversion model, wherein the set of physiological characteristic parameters includes at least one physiological characteristic parameter; and a first determining module, configured to determine plant species corresponding to the set of physiological characteristic parameters according to a preset plant database, wherein the plant database includes a set of physiological characteristic parameters corresponding to different plant species, wherein the controller further comprises:

a fourth processing module, configured to preprocess the hyperspectral data of plants to be studied, to obtain wavelet coefficients corresponding to the plants to be studied before the third pressing module obtains the set of physiological characteristic parameters corresponding to the plants to be studied according the wavelet coefficients corresponding to the plants to be studied and preset quantitative inversion model, wherein the plants to be studied are plants of known plant species; and a second determining module, configured to perform multiple regression fitting processing using the wavelet coefficients corresponding to the plants to be studied as independent variables, and the set of physiological characteristic parameters corresponding to the plants to be studied, obtained through the biochemistry experiments as dependent variables, to obtain the quantitative inversion model.

6. The system according to claim 5, wherein, the correction module is specifically configured to:

determine the corrected hyperspectral data according to the hyperspectral data, i.e. $DN=k*R+b$, wherein R is the hyperspectral data, and k and b are constant coefficients respectively.

7. The system according to claim 5, wherein, the first processing module comprises:

a first determining submodule, configured to determine a projection matrix P according to a spectral matrix, i.e. $X=XP+XQ+R$, wherein X is a matrix of the corrected hyperspectral data, P is a projection matrix for information that is useful for data prediction in the corrected hyperspectral data, Q is a projection matrix for information that is useless for data prediction in the corrected hyperspectral data, and R is a preset residual matrix; and a second determining submodule, configured to determine a orthogonalisation matrix according to the matrix X of the corrected hyperspectral data and the projection matrix P, i.e. X*=XP, and determine that the orthogonalisation matrix X* is the EPO processed hyperspectral data.

8. The system according to claim 5, wherein, the fourth processing module is specifically configured to:

perform atmospheric radiation correction for the hyperspectral data of plants to be studied by adopting Linear Regression method, to obtain corrected hyperspectral data of plants to be studied;

perform EPO processing for the corrected hyperspectral data of the plants to be studied, to obtain EPO processed hyperspectral data of the plants to be studied;

perform first order differential processing for the EPO processed hyperspectral data of the plants to be studied, to obtain hyperspectral data of the plants to be studied highlighting the absorption peak information; and perform discrete wavelet transform processing for the hyperspectral data of the plants to be studied highlighting the absorption peak information by adopting discrete wavelet transformation, to obtain wavelet coefficients corresponding to the plants to be studied.

\* \* \* \* \*